(12) United States Patent
Anderson et al.

(10) Patent No.: US 6,630,062 B1
(45) Date of Patent: Oct. 7, 2003

(54) POISON RESISTANT SENSOR

(75) Inventors: Conrad Harry Anderson, Davison, MI (US); Richard Frederick Beckmeyer, Davisburg, MI (US); William J. La Barge, Bay City, MI (US)

(73) Assignee: Delphi Technologies, Inc., Troy, MI (US)

( * ) Notice: Subject to any disclaimer, the term of this patent is extended or adjusted under 35 U.S.C. 154(b) by 195 days.

(21) Appl. No.: 09/631,911

(22) Filed: Aug. 4, 2000

(51) Int. Cl.$^7$ .................. G01N 27/407; B05D 5/00
(52) U.S. Cl. .................. 204/429; 204/426; 204/427; 427/58; 427/126.4
(58) Field of Search ................... 204/421–429

(56) References Cited

U.S. PATENT DOCUMENTS

| | | | |
|---|---|---|---|
| 3,811,899 A | 5/1974 | Stibbs et al. ............ 106/43 |
| 4,097,353 A | * | 6/1978 | Kishida et al. |
| 4,272,349 A | 6/1981 | Furutani et al. ........ 204/195 |
| 4,279,666 A | * | 7/1981 | Micheli |
| 5,252,314 A | 10/1993 | DeGuire et al. ........ 423/593 |
| 5,389,589 A | 2/1995 | Kharas ................... 501/127 |
| 5,395,406 A | 3/1995 | Clavenna et al. ........ 48/198 |
| 5,395,654 A | 3/1995 | Philipp et al. ........ 427/376.6 |
| 5,423,973 A | 6/1995 | Friese et al. ........... 204/426 |
| 5,522,979 A | * | 6/1996 | Tatumoto et al. |
| 5,593,558 A | 1/1997 | Sugino et al. .......... 204/429 |
| 5,593,654 A | 1/1997 | Decker, Jr. et al. ...... 423/625 |
| 5,639,929 A | 6/1997 | Bharadwaj et al. ...... 585/658 |
| 5,773,894 A | * | 6/1998 | Friese et al. |
| 5,837,634 A | 11/1998 | McLaughlin et al. .... 501/127 |
| 5,846,615 A | 12/1998 | Sharma et al. .......... 427/597 |
| 5,849,165 A | 12/1998 | Kojima et al. .......... 204/429 |
| 5,894,038 A | 4/1999 | Sharma et al. .......... 427/554 |

* cited by examiner

Primary Examiner—T. Tung
(74) Attorney, Agent, or Firm—Vincent A. Cichosz

(57) ABSTRACT

The poison resistant sensor comprises a sensing electrode (4) having a first and second side; a reference electrode (7) having a first and second side; an electrolyte (1) disposed between and in intimate contact with the first side of the sensing electrode and the first side of the reference electrode; a first side of a protective layer (3) disposed adjacent to the second side of the sensing electrode; and a protective coating (17), comprising alpha alumina and gamma alumina, disposed in physical contact with the second side of the protective layer.

30 Claims, 3 Drawing Sheets

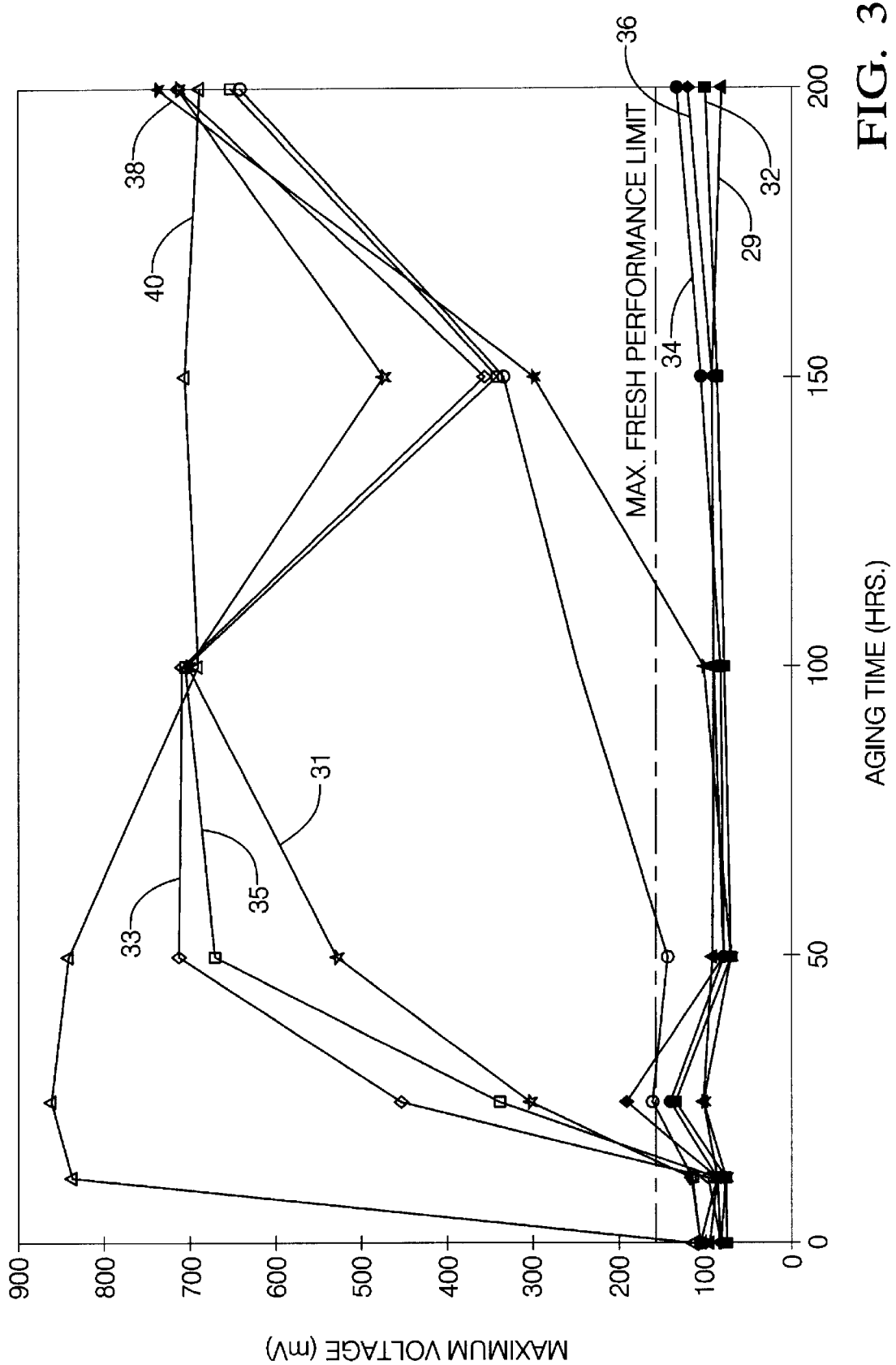

POISON RESISTANT SENSOR

TECHNICAL FIELD

The present invention relates to sensors and particularly, to a sensor with a metal oxide coating for resistance to poisoning.

BACKGROUND OF THE INVENTION

The automotive industry has used exhaust sensors for many years to detect the composition of exhaust gases such as oxygen, hydrocarbons, nitrous oxides and the like. For example, an oxygen sensor measures oxygen concentration in exhaust gases post combustion. This information is then utilized to control the operation of the engine, i.e. control air to fuel ratios, to enable improved performance and/or reduced emissions.

In a conventional sensor, the sensor comprises a first electrode capable of sensing an exhaust gas and a second electrode capable of sensing a reference gas with an ionically conductive solid electrolyte disposed therebetween. High temperatures and materials such as silicon, lead, and the like, present in engine components, can poison or otherwise damage the sensing electrode. In order to prevent poisoning/damage to the sensing electrode, a protective layer made of spinel or the like, has conventionally been applied to the sensing electrode. At protective layer thicknesses which retain the electrode performance, the silicon, lead, and other particles can pass through the layer and poison the electrode. At higher thicknesses which more effectively inhibit transmission of the poisoning material(s), the efficiency of the electrode is decreased. Furthermore, although the protective layer inhibits access of the poisoning particles to the electrode, the protective layer itself can become clogged, thereby also inhibiting passage of exhaust gases for sensing.

One conventional poison resistance technique comprised applying multiple layers of a heat-resistant metal oxide(s) over the electrode to form a protective layer. However, the multiple layers changed the performance of the sensor and only provided limited poison protection.

Accordingly, there remains a pressing need in the art for a sensor that is poison resistant for a longer period of time without any significant performance change.

SUMMARY OF THE INVENTION

The present invention relates to a sensor and a method for making the same. The sensor comprises: a sensing electrode having a first and second side and a first electrical lead in electrical communication with said sensing electrode; a reference electrode having a first and second side and a second electrical lead in electrical communication with said reference electrode; an electrolyte disposed between and in intimate contact with said first side of said sensing electrode and said first side of said reference electrode; and a first side of a protective layer disposed adjacent to said second side of said sensing electrode, wherein a second side of said protective layer has a protective coating, said protective coating comprising a mixture of alpha alumina and gamma alumina.

The method for making the sensor comprises: using a sensing electrode having a first and second side and a first electrical lead in electrical communication with said sensing electrode; using a reference electrode having a first and second side and a second electrical lead in electrical communication with said reference electrode; disposing an electrolyte between said first side of said sensing electrode and said first side of said reference electrode; disposing a first side of a protective layer adjacent to said second side of said sensing electrode; and disposing a protective coating comprising a mixture of alpha alumina and gamma alumina in physical contact with said protective layer.

BRIEF DESCRIPTION OF THE DRAWINGS

The present invention will now be described, by way of example, with reference to the following figures, which are meant to be exemplary, not limiting, and in which:

FIG. 3 is graph showing the siloxane poisoning test run at 400° C. with Ageing time on the X axis (hours) and Minimum Voltage on the Y axis in millivolts (mV).

DESCRIPTION OF THE PREFERRED EMBODIMENT

A protective coating for sensors, in particular oxygen sensors, is formed from a composition comprising alpha alumina and gamma alumina. Although described in connection with an oxygen sensor, it is understood that the sensor could be a nitrous oxide sensor, hydrogen sensor, hydrocarbon sensor, or the like. Furthermore, while oxygen is the reference gas used in the description disclosed herein, it should be understood that other gases could be employed as a reference gas.

The sensor comprises a sensing electrode capable of sensing an exhaust gas, a reference electrode capable of sensing a reference gas, an electrolyte disposed between and in intimate contact with a first side of the sensing electrode and a first side of the reference electrode, with a first side of a protective layer disposed adjacent to the second side of the sensing electrode, and the second side of the protective layer having a protective coating comprising alpha alumina and gamma alumina.

Figure 1:
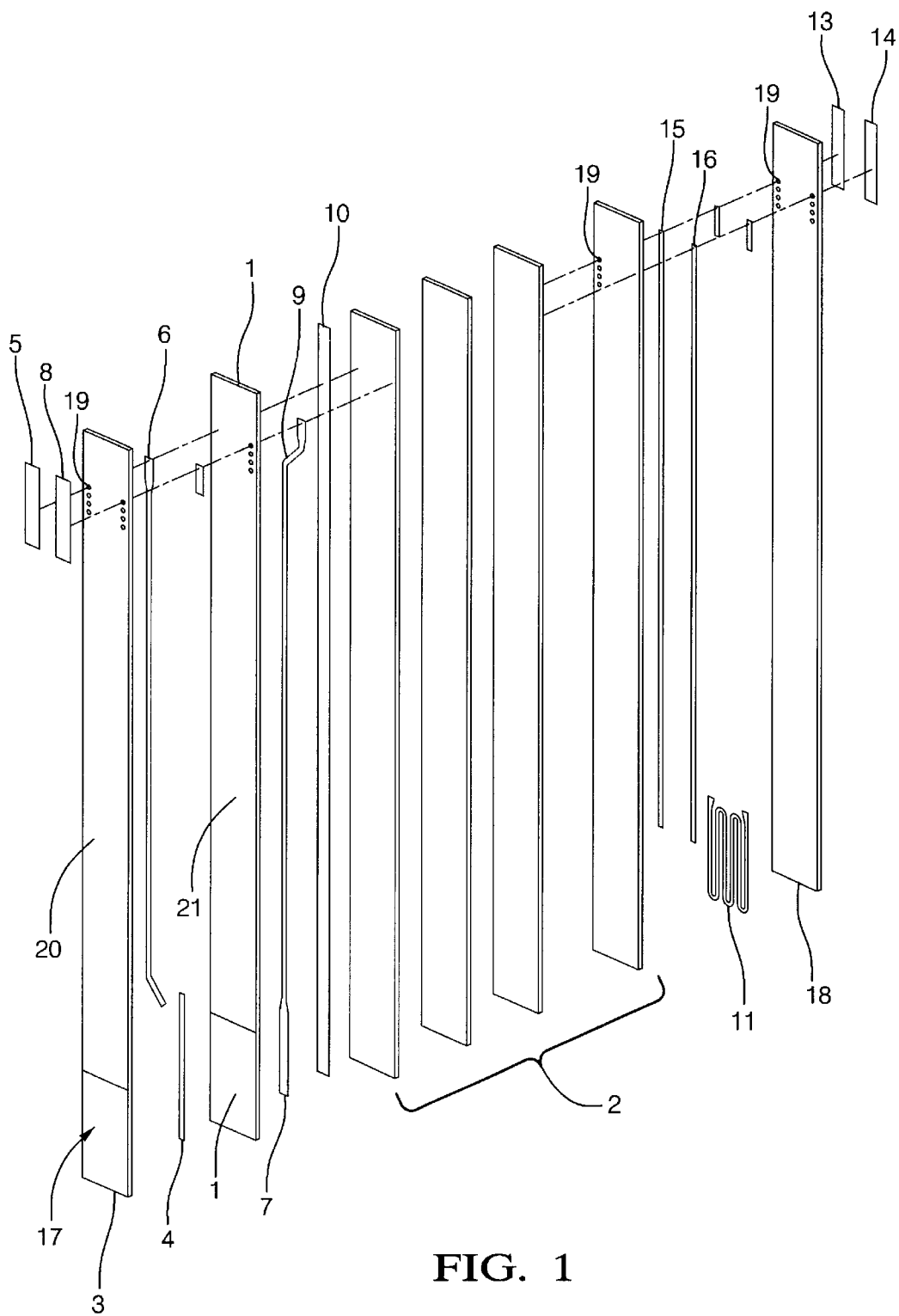
FIG. 1 is an example of an oxygen sensor.

Preferably, the sensor, according to one embodiment, is configured according to FIG. 1. FIG. 1 shows a sensor with an ionically conductive solid electrolyte (1), a sensing electrode (4) disposed in ionic communication with the solid electrolyte (1), and a porous protective layer (3) disposed on a side of the sensing electrode (4) opposite the solid electrolyte (1). On a second side of the solid electrolyte (1) is a reference electrode (7). The electrolyte (1) and porous protective layer (3) can be disposed adjacent to or as inserts within dielectric substrate layers (21, 20), respectively. On a second side of the reference electrode (7) can be support layers (2, 18), with a heater (11) disposed therebetween. Optionally, across the support layer (12) adjacent reference electrode (7) can be a reference chamber (10) typically formed using a fugitive material such as a carbon based material. The sensing electrode (4), reference electrode (7), and heater (11) are connected to contacts (5,8,13,14) on the outer sides of the sensor through vias (19) with leads (6,9,15,16) respectively.

The substrate layers (20,21), support layers (2, 18), beater, (11), contacts (5,8,13,14) and leads (6,9,15,16), and vias (19) can be composed of materials conventionally used in exhaust sensors. For example, the substrate layers (20,21), and the support layers (2,18) can comprise a dielectric material such as a metal oxide, e.g., alumina, while the heater(s) (11), leads (6,9,15,16), vias (19) and contacts (5,8,13,14) can comprise an electrically conductive metal, such as platinum, palladium, ruthenium, and the like, and other metal oxides and alloys and mixtures comprising at least one of the foregoing metals and metal oxides.

The solid electrolyte (1) can comprise any material conventionally employed as sensor electrolytes, including, but not limited to, zirconia which may optionally be stabilized with calcium, barium, yttrium, aluminum, lanthanum, cesium, gadolinium, and the like, as well as combinations comprising at least one of the foregoing. For example, the electrolyte can be alumina and yttrium stabilized zirconia.

Disposed on or adjacent to both sides of the electrolyte are electrodes (4,7). These electrodes can comprise any material conventionally employed in sensors, including metals such as platinum, palladium, osmium, rhodium, iridium, gold, and ruthenium; metal oxides such as zirconia, yttria, ceria, calcia, alumina and the like; other materials, such as silicon, and the like; and mixtures and alloys comprising at least one of the foregoing materials.

Disposed adjacent to the second side of the sensing electrode is a protective layer (3) comprising a metal oxide alone or in combination with one or more alkali, alkaline earth, rare earth, and/or other metal(s). Possible metal oxides include zirconia, alumina, magnesia, titania, silica, ferric oxide, chromic oxide, yttria, calcium oxide, and the like, and mixtures comprising at least one of the foregoing metal ozides. Possible alkali and alkaline earth metals comprise barium, calcium, potassium, sodium, and the like, as well as combinations comprising at least one of the foregoing alkali and alkaline earth metals, while the rare earth metals include lanthanum, neodymium, cerium, and the like, as well as combinations comprising at least one of the foregoing rare earth metals.

On at least the outer surface of the protective layer (3) is a protective coating (17). This protective coating (17), which may optionally coat all or a portion of the substrate layer (20) and/or support layer (18), is formed from a composition comprising a metal oxide. Possible metal oxides include zirconia, alumina, magnesia, titania, and the like, and mixtures comprising at least one of the foregoing metal oxides. Preferably, the coating comprises about 25 wt % to about 75 wt % gamma alumina, about 25 wt % to about 75 wt % alpha alumina, and optionally up to about 15 wt % binder; with about 35 wt % to about 65 wt % gamma alumina, about 35 wt % to about 65 wt % alpha alumina, and optionally up to about 10 wt % binder preferred; and about 45 wt % to about 55 wt % gamma alumina and about 45 wt % to about 55 wt % alpha alumina, and about 1 wt % to about 3 wt % binder especially preferred.

The gamma alumina may additionally comprise a stabilizer, such as an alkaline earth metal and/or a lanthanide metal, or a compound, oxide, or combination comprising at least one of the foregoing stabilizers. Some possible stabilizers include barium, lanthanum, cerium or the like, as well as compounds and oxides of these metals and combinations comprising at least one of the foregoing stabilizers. Preferably, the stabilized gamma alumina comprises up to about 20 wt % stabilizer, with up to about 15 wt % preferred, and about 1 wt % to about 6 wt % especially preferred.

The alpha alumina may also be stabilized such as with a metal, metal oxide, metal alkoxide, or the like. Coating the alpha alumina can inhibit the alpha alumina from "seeding" the transition of gamma alumina to alpha alumina. By having a dissimilar material in the grain boundary between alpha alumina particles and gamma alumina particles, the particles are much more resistant to sintering. Preferably, the alpha alumina is stabilized by coating the particles with an alkaline earth and/or lanthanide metal, metal oxide and/or metal alkoxide. Possible metals include barium, lanthanum, cerium, and the like, such as a barium organometallic, e.g., barium 2-ethylhexonoate which, when deposited on the alumina and then calcined creates barium coated alpha alumina particles.

The gamma alumina and alpha alumina preferably comprise agglomerates. Preferably, the agglomerate size of the gamma alumina is up to about 20 microns ($\mu$) or greater, with about $6\mu$ to about $14\mu$ agglomerate size preferred. Generally, the alpha alumina particle size is up to about $1\mu$, with about $0.3\mu$ to about $0.5\mu$ preferred. It is believed that the small alpha alumina size allows the alpha alumina to pack between the gamma alumina agglomerates. During use of the sensor, gas, unable to readily pass through the dense alpha alumina, passes through the gamma alumina agglomerates which filter out contaminates.

In addition to the gamma alumina and alpha alumina, the coating composition prepared for dipping the sensor may additionally comprise a binder. The binder, which can be employed in amounts of up to about 15 wt % or more, is typically employed in an amount of up to about 10 wt %, with about 1 wt % to about 3 wt % preferred. Possible binders comprise materials that will not adversely effect the protective properties of the protective coating. Preferably, the binder, upon sintering, will transform into alpha alumina or gamma alumina. Some possible binders comprise aluminum nitrate, aluminum hydroxide, and the like, as well as combinations comprising at least one of these binders.

The protective coating can be one or more layers having an overall thickness of up to or exceeding about $200\mu$, with a thickness of about 50 to about $150\mu$ preferred. The protective coating can be dense (e.g., a porosity less than about 5%), porous (e.g., a porosity greater than about 35%), or therebetween, with a coating having agglomerates of particles acting as filters for physical and chemical filtration preferred (e.g., a porosity of up to about 20% or so, with about 7% to about 14% preferred).

The protective coating can be applied to the protective layer in a conventional fashion. Some possible techniques include imbibing, spraying, spray coating, impregnating, painting, dipping, spin coating, vapor deposition, and the like. For example, a solution, suspension, ink, paste, slurry, or other type of mixture is prepared by mixing gamma alumina, alpha alumina, and/or binder in a sufficient amount of solvent to attain the desired viscosity. Some possible solvents include water, nitric acid, benzoic acid, acetic acid, citric acid, or the like, as well as combinations comprising at least one of the foregoing. Preferably, the mixture comprises a sufficient amount of alumina to attain the desired alumina loading in the final product. Generally, about 45 wt % solids or greater, balance solvent, is employed, wherein the solids includes the gamma alumina, alpha alumina, and binder, with about 50 wt % to about 55 wt % solids preferred, and about 52 wt % to about 54 wt % solids especially preferred. Alternatively a lower solids concentration can be employed, e.g., less than about 45 wt %, wherein multiple applications of the protective coating to attain the desired loading.

Prior to application of the slurry, the alumina is preferably milled using known milling techniques (e.g., dry milling, wet milling, etc.), to attain the desired mean alpha and gamma alumina particles sizes. Any low efficiency milling method can be used, with dry milling of powders acceptable, and mixing coarse gamma alumina, such as CONDEA Vista SCFA-100, with fine alpha alumina without milling also acceptable. Once the slurry having the desired viscosity and composition is prepared, the slurry can then be applied to the desired area of the sensor. Typically the protective coating is applied to the protective layer (3) disposed adjacent to the sensing electrode and optionally to the support layers (20, 18). (see FIG. 1) The coated sensor can then be calcined as is conventionally known in the art. Typically the sensor is calcined at temperatures of about 1,000° C. or so.

The following examples are provided to further illustrate the present invention and are not intended to limit the scope thereof.

EXAMPLES

The following examples were used to prepare exhaust sensors, each having a platinum containing electrode, yttria doped zirconia electrolyte, alumina support layers, an alumina and zirconia protective layer, and a 49 wt % gamma alumina, 51 wt % alpha alumina protective coating.

Example 1

An electrolyte was disposed between two alumina supports with a platinum electrode screen printed on each support such that the electrodes were in intimate contact with the electrolyte. Electrical leads were also disposed across the electrolyte from the electrodes to contacts (vias) disposed at an end of the sensor opposite the electrodes. The protective layer was then oriented in physical contact with one of the electrodes (the sensing electrode). The other electrode was disposed in contact with a series of alumina support layers, wherein the support layer in direct contact with the electrode had a fugitive material screen printed thereon. On the opposite side of the support layers was another protective layer with a heater disposed therebetween.

A thixotropic slurry was then prepared by mixing 4,900 grams (g) of alpha alumina, 4,900 g of gamma alumina, and 200 g of aluminum nitrate (binder) with water. The sensor was then dipped in the slurry and dried for 10 minutes at 80° C. Once the layer was dry, the sensor was calcined at a temperature of at least 350° C. for 15 minutes.

Example 2

An electrolyte was disposed between two alumina supports with a platinum electrode screen printed on each support such that the electrodes were in intimate contact with the electrolyte. Electrical leads were also disposed across the electrolyte from the electrodes to contacts disposed at an end of the sensor opposite the electrodes. A protective layer, disposed adjacent to a substrate layer, was then oriented in physical contact with one of the electrodes (the sensing electrode). The other electrode was disposed in contact with a series of alumina support layers, wherein the support layer in direct contact with the electrode had a fugitive material screen printed thereon. On the opposite side of the support layers was another support layer with a heater disposed therebetween.

Barium coated alpha alumina was prepared by adding 5,000 g of Alcoa A16-SG alpha alumina to a 2 liter solution of 6 wt % barium 2-ethylhexanoate in toluene. The mixture was stirred for 20 minutes. The liquid was filtered off leaving alpha alumina particles with a thin coating of barium 2-ethylhexanoate. The particles were then calcined to 500° C. for 1 hour.

The thixotropic slurry was then prepared by adding 4,900 g of the barium coated alpha alumina, 4,900 g of gamma alumina doped with 3 wt % barium (specifically CONDEA Vista Puralox® SCFA 140 B3), 200 g of aluminum nitrate crystals, and 9,600 g of distilled water. The mixture was high shear mixed for 20 minutes. The resulting slurry was applied to a sensor by dipping the sensor into the slurry using a dipping machine.

Figure 2:
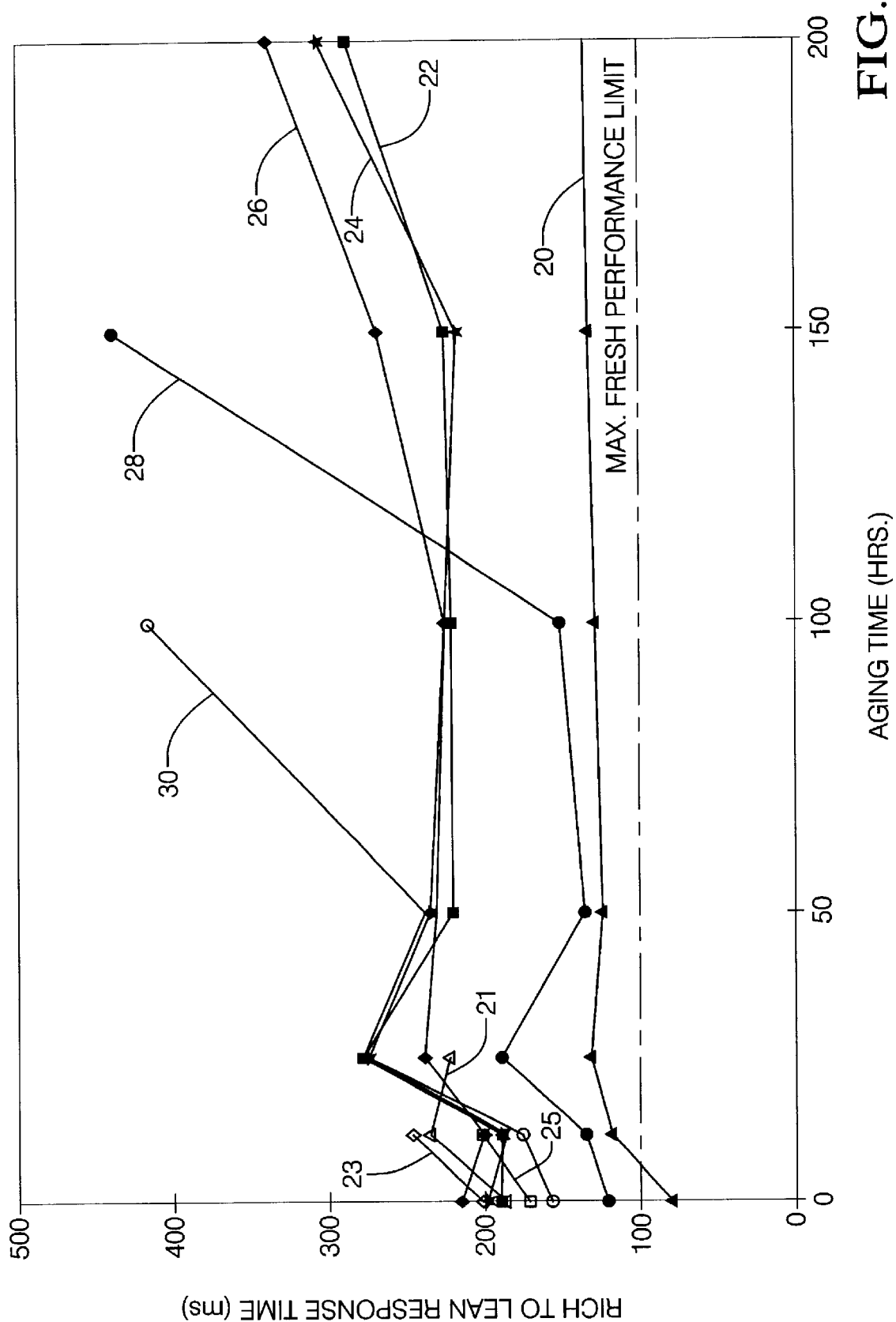
FIG. 2 is a graph showing the siloxane poisoning test run at 400° C. with Ageing time on the X axis (hours) and Rich to Lean Response Time on the Y axis in milliseconds (ms).

FIGS. 2 and 3 graphically illustrate siloxane poisoning tests conducted at 400° C. for 200 hours. As can be seen from FIG. 2, the sensor prepared in accordance with the above Example 1, represented by line 20 (flame sprayed spinel then gamma/alpha (g/a) alumina coating), maintained a substantially better rich to lean response time, about or below about 130 milliseconds (ms) for the entire 200 hours. The other sensors that maintained a better response time than the conventional sensors were those represented by lines 22, 24, 26, which maintained a response time of about 300 ms or less for the 200 hour test. These sensors comprised plasma sprayed spinel ($MgAl_2O_4$) (300μ, 200μ, and 100μ, respectively), coated with g/a alumina. Data was not recorded after about 25 hours for sensors with no protective coating, represented by lines 21 (200 micron (g) spinel), 23 (100μ spinel), 25 (300μ spinel), because the parts would not switch. Sensors with two separate coatings, line 28 (dense gamma alumina coating beneath a coarse gamma alumina coating); and the sensor with one layer coating line 30 (100μ dense gamma alumina), could not maintain a response time below 250 ms greater than 50 hours. (see FIG. 2).

Furthermore, as is illustrated in FIG. 3, the voltage required by the sensors disclosed herein, lines 29 (flame sprayed spinel then (g/a) alumina coating), 32 (300μ plasma sprayed spinel then g/a alumina coating), 34 (200μ plasma sprayed spinel then g/a alumina coating), 36 (100μ plasma sprayed spinel then g/a alumina coating), essentially remains below 150 millivolts (mV), and mostly below 100 mV, for the entire 200 hours. In contrast, with the exception of the sensor with the dense gamma alumina coating beneath a coarse gamma alumina coating, line 38, which exceeded 150 mV after 115 hours, the sensors without the g/a alumina coating exceeded 150 mV after 25 hours; e.g., lines 31 (200μ plasma sprayed spinel), 33 (100μ plasma sprayed spinel), 35 (300μ plasma sprayed spinel), 40 (no coating), and 42 (100μ dense gamma alumina).

This invention overcomes some of the shortcomings that exist in the prior art. This sensor has a single layer protective coating demonstrating better resistance to poisoning, e.g., maintaining a voltage below about 200 mV, with a voltage below about 150 mV preferred, and a voltage below about 100 mV especially preferred. This sensor is capable of maintaining this voltage for at least about 200 hours, with greater than about 250 hours preferred, and greater than about 400 hours especially preferred. For example, when this sensor with the protective coating was tested over a flame sprayed spinel, the sensor could last for at least two hundred hours of poisoning without any performance change. Similarly, when this sensor was tested over a plasma sprayed spinel layer or over cofired alumina, the sensor could last for at least one hundred and fifty hours of poisoning with substantially no performance change.

The sensor disclosed herein comprises a combination of coarse (gamma) and fine (alpha) alumina. The coarse gamma alumina allows the sensor to "breath", while the fine alpha alumina enables good packing against the larger coarse particles. Essentially, gas transfer is substantially inhibited, or even prevented, through fine dense packed material, thereby only allowing gas flow through large coarse particles.

In contrast to prior art sensors comprising alumina coatings, the coating of this sensor is substantially free of surface imperfections. Surface imperfections enabling poison paths can be created by bubbles, which can break. Bubbles can be formed either by foaming of the slurry as it is being processed or by the escaping of air from other parts of the sensor. The slurry described herein does not foam in the processing equipment and trapped air from other parts of the sensor cannot pass through the slurry because of very high surface tension from the presence of the binder. Since no bubbles are created, no defects are formed.

Some of the other advantages of this sensor include an easier manufacturing process, due to the thixotropic nature of the slurry; a harder coating, due to the presence of aluminum nitrate only and not alumina sol which makes coatings softer; and better poison protection for the sensor, since the gas phase poisons are "sieved" through the highly reactive gamma alumina.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A sensor, comprising:
  a sensing electrode having a first and second side and a first electrical lead in electrical communication with said sensing electrode;
  a reference electrode having a first and second side and a second electrical lead in electrical communication with said reference electrode;
  an electrolyte disposed between and in intimate contact with said first side of said sensing electrode and said first side of said reference electrode; and
  a first side of a protective layer disposed adjacent to said second side of said sensing electrode, wherein said protective layer has a protective coating, said protective coating comprising a mixture of alpha alumina particles having a size up to about 1 micrometer, and gamma alumina agglomerates, wherein said alpha alumina particles pack between said gamma alumina agglomerates.

2. A sensor of claim 1, wherein said protective layer is porous.

3. A sensor of claim 1, wherein said gamma alumina has an agglomerate size of up to about 20$\mu$.

4. A sensor of claim 3, wherein said agglomerate size is about 6$\mu$ to about 14$\mu$.

5. A sensor of claim 1, wherein said protective coating is a single layer.

6. A sensor of claim 1, wherein said protective coating comprises about 25 wt % to about 75 wt % gamma alumina and about 25 wt % to about 75 wt % alpha alumina.

7. A sensor of claim 6, wherein said protective coating comprises about 35 wt % to about 65 wt % gamma alumina and about 35 wt % to about 65 wt % alpha alumina.

8. A sensor of claim 7, wherein said protective coating comprises about 45 wt % to about 55 wt % gamma alumina and about 45 wt % to about 55 wt % alpha alumina.

9. A sensor of claim 1, wherein said alpha alumina has a particle size of about 0.3$\mu$ to about 0.5$\mu$.

10. A sensor of claim 1, wherein said gamma alumina and/or said alpha alumina comprises a stabilizer selected from the group consisting of an alkaline earth metal, a lanthanide metal, and combinations comprising at least one of the foregoing stabilizers.

11. A sensor of claim 10, wherein said stabilizer is selected from the group consisting of barium, lanthanum, cerium, oxides and compounds of barium, lanthanum, cerium, and combinations comprising at least one of the foregoing stabilizers.

12. A sensor of claim 10, wherein said stabilizer is present in an amount of up to about 20 wt %.

13. A sensor of claim 12, wherein said stabilizer is present in an amount of up to about 15 wt %.

14. A sensor of claim 13, wherein said stabilizer is present in an amount of about 1 wt % to about 6 wt %.

15. A sensor of claim 1, wherein said alpha alumina particles have a smaller size than said gamma alumina agglomerates.

16. A method for manufacturing a sensor, comprising:
  disposing an electrolyte between a first side of a sensing electrode and a first side of a reference electrode;
  disposing a first side of a protective layer adjacent to a second side of said sensing electrode; and
  disposing a protective coating comprising a mixture of alpha alumina particles having a size up to about 1 micrometer, and gamma alumina agglomerates, in physical contact with said protective layer, such that said alpha alumina particles pack between said gamma alumina agglomerates.

17. A method for manufacturing a sensor as in claim 16, wherein said gamma alumina and/or said alpha alumina further comprise a stabilizer.

18. A method for manufacturing a sensor as in claim 17, wherein said stabilizer is selected from the group consisting of an alkaline earth metal, a lanthanide metal, and combinations comprising at least one of the foregoing stabilizers.

19. A method for manufacturing a sensor as in claim 18, wherein said stabilizer is selected from the group consisting of barium, lanthanum, cerium, oxide and compounds of barium, lanthanum, cerium, and combinations comprising at least one of the foregoing stabilizers.

20. A method for manufacturing a sensor as in claim 18, wherein said stabilizer is present in an amount of up to about 20 wt %.

21. A method for manufacturing a sensor as in claim 20, wherein said stabilizer is present in an amount of up to about 15 wt %.

22. A method for manufacturing a sensor of claim 16, wherein said alpha alumina particles have a smaller size than said gamma alumina agglomerates.

23. A method for manufacturing a sensor of claim 16, wherein disposing said protective coating comprises:
  mixing about 25 wt % to about 75 wt % gamma alumina and about 25 wt % to about 75 wt % alpha alumina with a liquid to form a mixture; and
  applying the mixture to said sensor.

24. A method of manufacturing a sensor of claim 23, comprising mixing about 35 wt % to about 65 wt % gamma alumina and about 35 wt % to about 65 wt % alpha alumina.

25. A method for manufacturing a sensor as in claim 24, comprising mixing about 45 wt % to about 55 wt % gamma alumina and about 45 wt % to about 55 wt % alpha alumina.

26. A method for manufacturing a sensor as in claim 16, comprising mixing a binder with said alpha alumina and said gamma alumina.

27. A method for manufacturing a sensor as in claim 26, wherein said binder is selected from the group consisting of aluminum nitrate and aluminum hydroxide, and mixtures comprising at least one of the foregoing.

28. A method for manufacturing a sensor as in claim 27, wherein said mixture comprises ump to about 15 wt % binder.

29. A method for manufacturing a sensor as in claim 28, wherein said mixture comprises up to about 10 wt % binder.

30. A method for manufacturing a sensor as in claim 29, wherein said mixture comprises about 1 wt % to about 3 wt % binder.

* * * * *